US010155978B2

(12) United States Patent
Ma et al.

(10) Patent No.: US 10,155,978 B2
(45) Date of Patent: Dec. 18, 2018

(54) MULTI-CHANNEL FLUORESCENCE DETECTION DEVICE

(71) Applicant: Delta Electronics Int'l (Singapore) Pte Ltd, Singapore (SG)

(72) Inventors: Bo Ma, Singapore (SG); Song-Bin Huang, Singapore (SG); Jei-Yin Yiu, Singapore (SG); Hui Wang, Singapore (SG)

(73) Assignee: DELTA ELECTRONICS INT'L (SINGAPORE) PTE LTD, Singapore (SG)

( * ) Notice: Subject to any disclaimer, the term of this patent is extended or adjusted under 35 U.S.C. 154(b) by 79 days.

(21) Appl. No.: 15/611,433

(22) Filed: Jun. 1, 2017

(65) Prior Publication Data

US 2018/0127805 A1 May 10, 2018

(30) Foreign Application Priority Data

Nov. 8, 2016 (SG) .......................... 10201609334W

(51) Int. Cl.
| | | |
|---|---|---|
| *B01L 7/00* | (2006.01) | |
| *C12Q 1/686* | (2018.01) | |
| *G01N 21/03* | (2006.01) | |
| *G01N 21/64* | (2006.01) | |

(52) U.S. Cl.
CPC ................ *C12Q 1/686* (2013.01); *B01L 7/52* (2013.01); *G01N 21/645* (2013.01);
(Continued)

(58) Field of Classification Search
CPC ............... B01L 7/52; B01L 2300/1822; B01L 2300/0654; B01L 2200/028;
(Continued)

(56) References Cited

U.S. PATENT DOCUMENTS

| | | |
|---|---|---|
| 6,246,525 B1 | 6/2001 | Ikami |
| 6,498,690 B2 | 12/2002 | Ramm et al. |

(Continued)

*Primary Examiner* — Gautam Prakash
(74) *Attorney, Agent, or Firm* — Kirton McConkie; Evan R. Witt

(57) ABSTRACT

The multi-channel fluorescence detection device includes an illumination module, plural heating chambers, a detection module and a transmission module. The illumination module includes at least one light source, plural different types of excitation filters, and a first rotational drum, wherein the light source provides a broad band illumination, each of the excitation filters passes light at a particular band width for exciting a targeted fluorescent probe, and the first rotational drum drives the excitation filters. The plural heating chambers are adapted for accommodating PCR tubes having samples and the targeted fluorescent probes. The detection module includes plural different types of emission filters, a second rotational drum and at least one photo-detector, wherein each of the emission filters passes light at a particular band width, the second rotational drum drives the emission filters, and the photo-detector receives fluorescent signals and converts the fluorescent signals to electrical signals. The transmission module includes an actuator connecting with the first and the second rotational drums to drive rotations of the first and the second rotational drum simultaneously for switching and synchronizing the excitation filters and the emission filters to match specific wavelengths of the targeted fluorescent probes.

19 Claims, 11 Drawing Sheets

(52) U.S. Cl.
CPC .... *G01N 21/6428* (2013.01); *B01L 2200/025* (2013.01); *B01L 2200/028* (2013.01); *B01L 2300/0654* (2013.01); *B01L 2300/1822* (2013.01); *G01N 21/0332* (2013.01); *G01N 2021/6419* (2013.01); *G01N 2021/6421* (2013.01); *G01N 2021/6439* (2013.01); *G01N 2021/6471* (2013.01); *G01N 2201/062* (2013.01); *G01N 2201/068* (2013.01); *G01N 2201/0633* (2013.01); *G01N 2201/0638* (2013.01)

(58) Field of Classification Search
CPC .......... B01L 2200/025; G01N 21/6428; G01N 21/645; G01N 2021/6471; G01N 2201/0633; G01N 2201/062; G01N 2021/6439; G01N 2021/6421; G01N 2201/068; G01N 2021/6419; G01N 21/0332; G01N 2201/0638; C12Q 1/686
See application file for complete search history.

(56) References Cited

U.S. PATENT DOCUMENTS

| | | |
|---|---|---|
| 6,746,864 B1 | 6/2004 | McNeil et al. |
| 6,852,986 B1 | 2/2005 | Lee et al. |
| 6,940,598 B2 | 9/2005 | Christel et al. |
| 6,982,166 B2 | 1/2006 | Sandell |
| 7,015,484 B2 | 3/2006 | Gillispie et al. |
| 7,148,043 B2 | 12/2006 | Kordunsky et al. |
| 7,273,749 B1 | 9/2007 | Wittwer et al. |
| 7,289,217 B2 | 10/2007 | Boege et al. |
| 7,315,376 B2 | 1/2008 | Bickmore, Jr. et al. |
| 7,369,227 B2 | 5/2008 | Gutekunst et al. |
| 7,370,994 B2 | 5/2008 | Li |
| 7,663,750 B2 | 2/2010 | Bahatt et al. |
| 7,687,260 B2 | 3/2010 | Gutekunst |
| 7,700,928 B2 | 4/2010 | Rasnow et al. |
| 7,749,736 B2 | 7/2010 | Kordunsky et al. |
| 8,029,733 B2 | 10/2011 | Chang et al. |
| 8,278,114 B2 | 10/2012 | Gambini et al. |
| 8,441,629 B2 | 5/2013 | Kolesnychenko et al. |
| 8,557,569 B2 | 10/2013 | Boege et al. |
| 8,865,473 B2 | 10/2014 | Gambini et al. |
| 8,900,828 B2 | 12/2014 | Smith et al. |
| 8,921,098 B2 | 12/2014 | Gambini et al. |
| 8,987,685 B2 | 3/2015 | Fawcett et al. |
| 9,080,207 B2 | 7/2015 | Handique et al. |
| 9,096,892 B1 | 8/2015 | Klemer et al. |
| 2001/0046050 A1 | 11/2001 | Hoyt |
| 2003/0011772 A1 | 1/2003 | Abe et al. |
| 2004/0178357 A1 | 9/2004 | King |
| 2005/0133724 A1 | 6/2005 | Hsieh et al. |
| 2006/0289786 A1 | 12/2006 | Taylor et al. |
| 2007/0114444 A1 | 5/2007 | Reid et al. |
| 2008/0277595 A1 | 11/2008 | Lundquist et al. |
| 2009/0009767 A1 | 1/2009 | Boege et al. |
| 2014/0273181 A1 | 9/2014 | Abbott et al. |
| 2014/0283945 A1 | 9/2014 | Jones et al. |
| 2015/0232916 A1 | 8/2015 | Rasmussen et al. |

# MULTI-CHANNEL FLUORESCENCE DETECTION DEVICE

FIELD OF THE INVENTION

The present invention relates to a fluorescence detection device, and more particularly to a multi-channel fluorescence detection device.

BACKGROUND OF THE INVENTION

Due to the requirement of retrieving a particular segment of DNA in large quantities for different purposes, scientists need an efficient way to meet their goals. Polymerase chain reactions (PCR) is one of the cost-effective and time-saving techniques which could provide billion copies of specific DNA segments in short period of time. PCR technique could be applied in many fields, such as diagnosis of diseases in hospitals and biological research institutes, identification of bacteria and viruses, detection and monitoring of diseases, genomic mutation and cancer biomarkers, inspection of environmental hazards, investigation of criminals, and so on. PCR technique only requires small amount of DNA samples extracted from blood or tissues. By utilizing fluorescent dye into the nucleic acids solutions, the amplified DNA segments could be detected through the fluorescent molecules.

Dyes and fluorescence detection technique is one of the widely adopted techniques to simultaneously detect and analyze whether the targeted nucleic acids exist in a batch of biological samples. When fluorescent signals emitted from the targeted nucleic acids which possess DNA-binding dyes or fluorescein-binding probes due to the excitation illuminated at specific wavelength, this signal indicates that the targeted nucleic acids exist. This technique has been employed for the novel PCR technique, which is called real time PCR or qPCR. Comparing to the conventional PCR technique which is end-point PCR detection, qPCR is the early-phase PCR detection with higher sensitivity and better precision. Therefore, a tool as an optical device is necessary for qPCR detection technique. The optical device has to provide a light source for exciting fluorescent probes at their specific wavelengths, and in the meanwhile, it detects the fluorescent signals emitted from the probes.

The fluorescence detection systems have been well developed in many fields, such as the application of fluorescence spectroscopy and fluorescence microscopy. By utilizing a single white light source with a set of filters and optical components, single color fluorescent probes could be easily applied. However, when the fluorescent probes with different colors are required in an assay or multiple fluorescent probes are distributed laterally for detection, it drastically increased the complexity of the fluorescence detection device, and the requirements are difficult to suffice. Moreover, even if the requirements are met, this kind of fluorescence detection device in the market is bulky and heavy, and misalignment between light sources, moveable PCR samples and detectors are also an issue.

In light of the requirements and the issues addressed above, there is a need of providing an improved fluorescence detection device for multi-color qPCR application.

SUMMARY OF THE INVENTION

An object of the present invention is to provide a multi-channel fluorescence detection device for minimizing the size and the weight of the device, and still providing superior performance for multi-color qPCR application.

According to an aspect of the present invention, there is provided a multi-channel fluorescence detection device including an illumination module, plural heating chambers, a detection module and a transmission module. The illumination module includes at least one light source, plural different types of excitation filters, and a first rotational drum, wherein the light source provides a broad band illumination, each of the excitation filters passes light at a particular band width for exciting a targeted fluorescent probe, and the first rotational drum drives the excitation filters. The plural heating chambers are adapted for accommodating PCR tubes having samples and the targeted fluorescent probes. The detection module includes plural different types of emission filters, a second rotational drum and at least one photo-detector, wherein each of the emission filters passes light at a particular band width, the second rotational drum drives the emission filters, and the photo-detector receives fluorescent signals and converts the fluorescent signals to electrical signals. The transmission module includes an actuator connecting with the first and the second rotational drums to drive rotations of the first and the second rotational drum simultaneously for switching and synchronizing the excitation filters and the emission filters to match specific wavelengths of the targeted fluorescent probes.

In an embodiment, the light source is a white light LED.

In an embodiment, the illumination module further comprises at least one collimating lens located between the light source and the excitation filter.

In an embodiment, the excitation filter and the emission filer are band pass filters.

In an embodiment, the illumination module further includes a support and a control circuit board, the light source is mounted on the control circuit board, and the control circuit board is mounted on the support.

In an embodiment, the illumination module further comprises at least one converging lens mounted between the excitation filter and the heating chamber. The converging lens is mounted on a lens holder sitting on a top of the heating chambers and is a bi-convex lens.

In an embodiment, each of the illumination module and the detection module further comprises plural filter mounts, and the same type of excitation filters or emission filters are installed in the same filter mount. Each of the first and the second rotational drum is substantially shaped as an octagonal column, and comprises a position stop disposed on a side panel thereof. The transmission module further comprises a position plate configured to be against the position stops of the first and the second rotational drums for securing initial positions of the first and the second rotational drums.

In an embodiment, the plural heating chambers are positioned linearly for batch process.

In an embodiment, the multi-channel fluorescence detection device further comprises a thermoelectric cooling heater for heating the PCR tubes.

In an embodiment, the detection module further comprises at least one converging lens mounted between the heating chamber and the emission filter.

In an embodiment, the detection module further comprises at least one converging lens mounted between the emission filter and the photo-detector.

In an embodiment, the detection module further includes an electromagnetic (EMI) shielding and grounding structure covering the photo-detector.

In an embodiment, the actuator of the transmission module is a step motor mounted behind the light source, and the step motor rotates 45 degree one at a time.

In an embodiment, the transmission module further comprises a gear and a rack.

According to another aspect of the present invention, there is provided a multi-channel fluorescence detection device including an illumination module, plural heating chambers, a detection module and a transmission module. The illumination module includes at least one light source, plural different types of excitation filters, and a first carrier, wherein the light source provides a broad band illumination, each of the excitation filters passes light at a particular band width for exciting a targeted fluorescent probe, and the first carrier carries the excitation filters. The plural heating chambers are adapted for accommodating PCR tubes having samples and the targeted fluorescent probes. The detection module includes plural different types of emission filters, a second carrier, and at least one photo-detector, wherein each of the emission filters passes light at a particular band width, the second carrier carries the emission filters, and the photo-detector receives fluorescent signals and converts the fluorescent signals to electrical signals. The transmission module includes an actuator connecting with the first and the second carriers to drive the first and the second carriers simultaneously for switching and synchronizing the excitation filters and the emission filters to match specific wavelengths of the targeted fluorescent probes.

The above objects and advantages of the present invention become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

The present invention provides a multi-channel fluorescence detection device which is an optical module sequentially illuminating lights with four different colors on multiple fluorescent samples arranged in linear position. During the qPCR amplification process, this device provides light source with different colors to excite different fluorescent probes, and detect specific fluorescent signal emitted from the probes by rotating excitation and emission filters which are driven by two rotational drums simultaneously.

Figure 1:
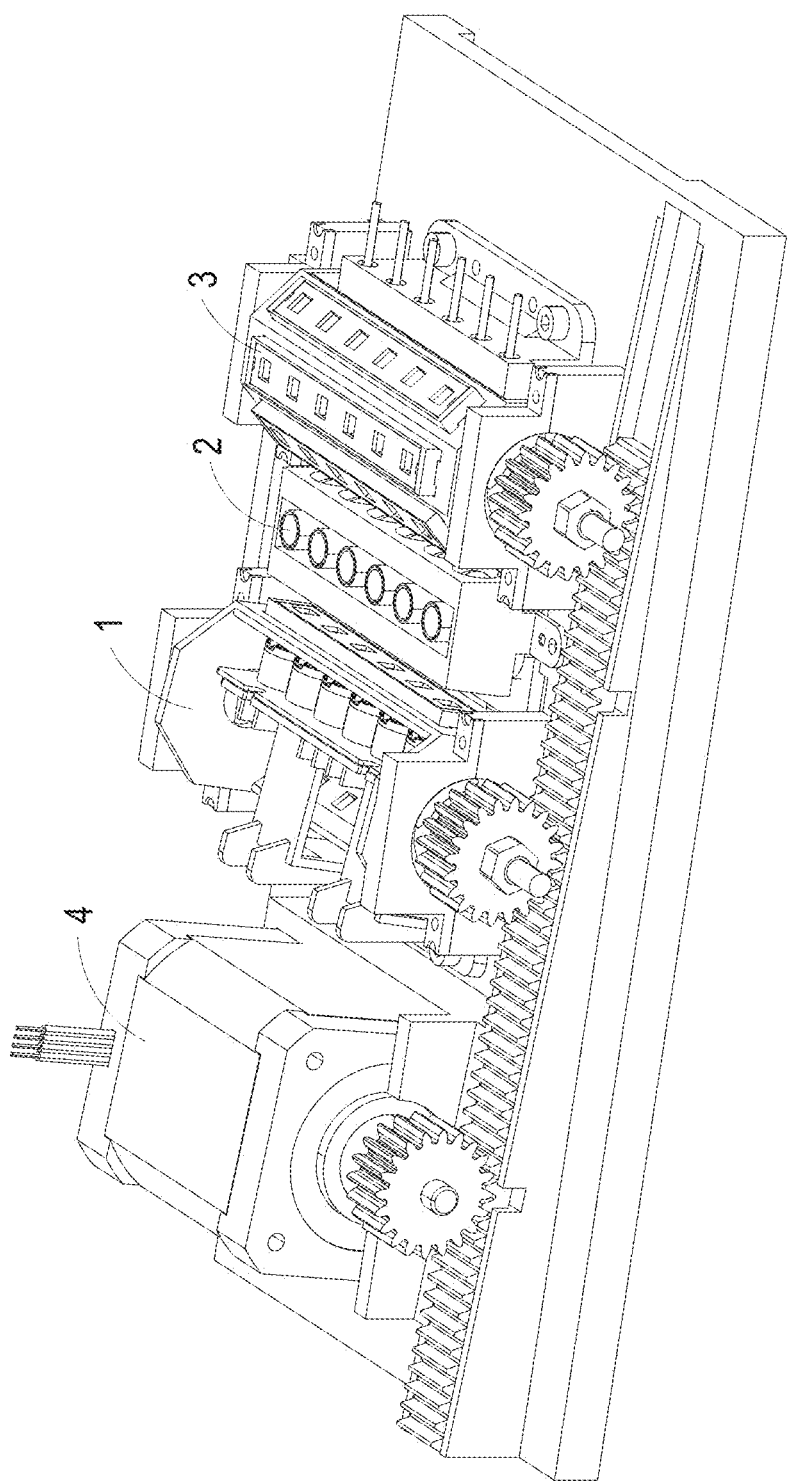
FIG. 1 shows a schematic view of the multi-channel fluorescence detection device according to a preferred embodiment of the present invention.
Figure 2:
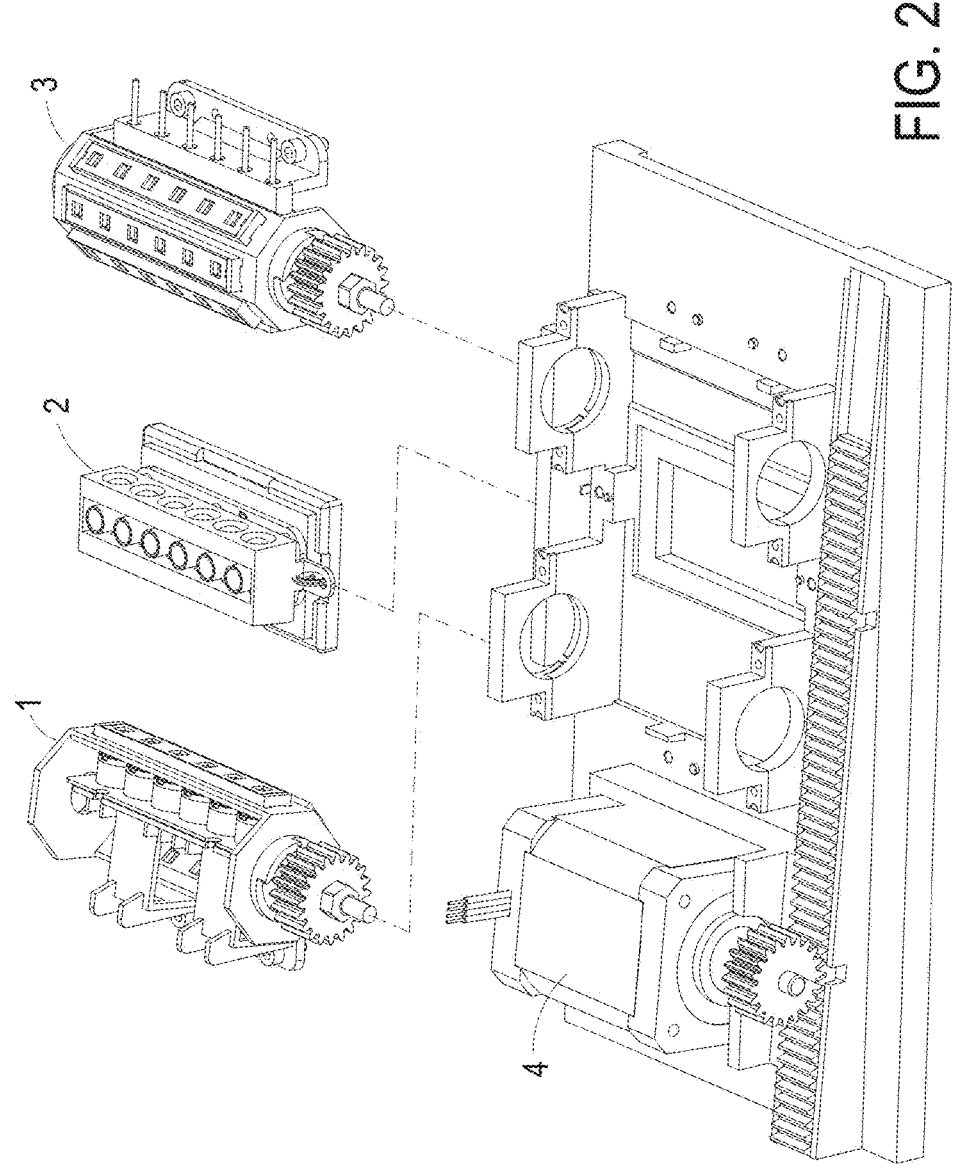
FIG. 2 shows an exploded view of the multi-channel fluorescence detection device of FIG. 1.
Figure 3:
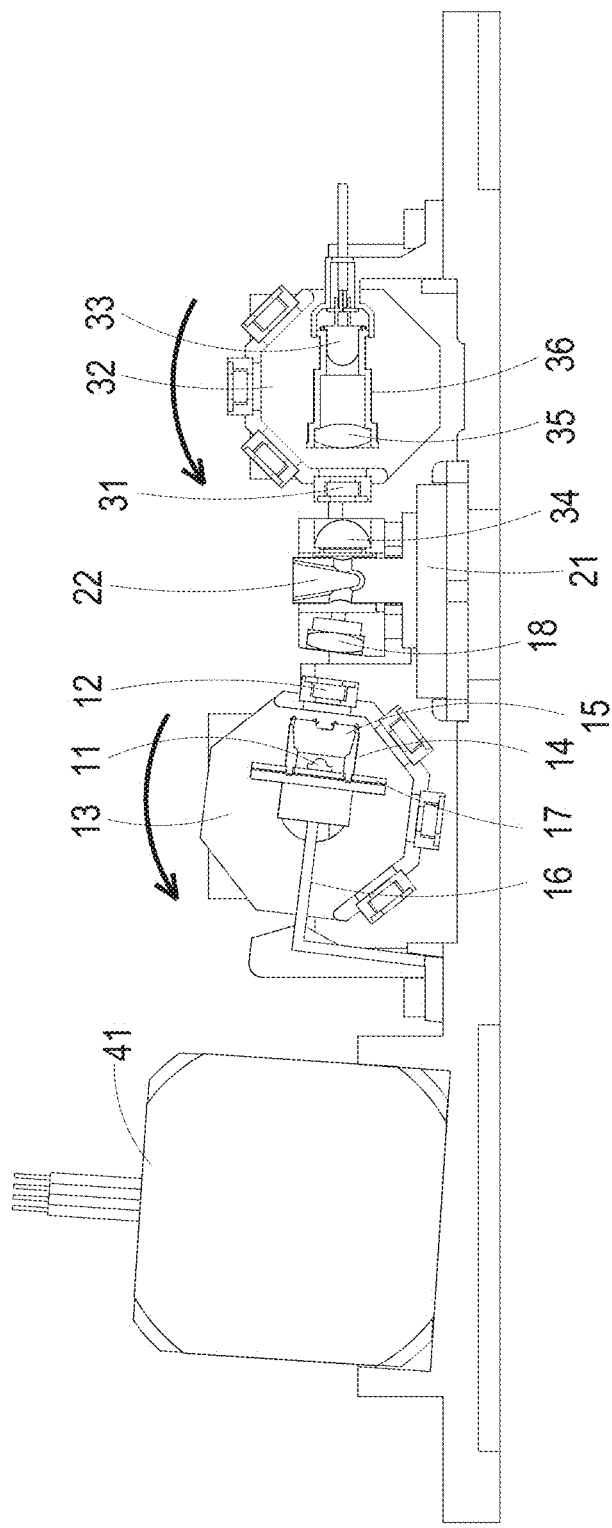
FIG. 3 shows a cross-sectional view of the multi-channel fluorescence detection device of FIG. 1.

Please refer to FIGS. 1-3, wherein FIG. 1 shows a schematic view of the multi-channel fluorescence detection device according to a preferred embodiment of the present invention, FIG. 2 shows an exploded view of the multi-channel fluorescence detection device of FIG. 1, and FIG. 3 shows a cross-sectional view of the multi-channel fluorescence detection device of FIG. 1. As shown in FIGS. 1-3, the multi-channel fluorescence detection device mainly includes an illumination module 1, a heating module 2, a detection module 3 and a transmission module 4. The illumination module 1 is located in front of the heating module 2, and the detection module 3 is located behind the heating module 2, and the transmission module 4 is connected with the illumination module 1 and the detection module 3 through gear and rack transmission.

The illumination module 1 includes at least one light source 11, plural different types of excitation filters 12, and a first carrier 13, wherein the light source 11 provides a broad band illumination, each of the excitation filters 12 passes light at a particular band width for exciting a targeted fluorescent probe, and the first carrier 13 carries the excitation filters 12. The heating module 2 includes a heater 21 and plural heating chambers 22, wherein the heater 21 provides thermal control for PCR amplification, and the plural heating chambers 22 accommodate PCR tubes having samples and the targeted fluorescent probes. The detection module 3 includes plural different types of emission filters 31, a second carrier 32, and at least one photo-detector 33, wherein each of the emission filters 31 passes light at a particular band width, the second carrier 32 carries the emission filters 31, and the photo-detector 33 receives fluorescent signals and converts the fluorescent signals to electrical signals. The excitation filters 12 and the emission filters 31 are paired into plural sets for detecting light source with different colors. The transmission module 4 includes an actuator, which is preferably a step motor 41, connecting with the first carrier 13 and the second carrier 32 to drive rotations of the first carrier 13 and the second carrier 32 simultaneously for switching and synchronizing the excitation filters 12 and the emission filters 31 to match specific wavelengths of the targeted fluorescent probes. In an embodiment, the first carrier 13 comprises a first rotational drum for driving and switching the excitation filters 12. The second carrier 32 comprises a second rotational drum for driving and switching the emission filters 31. The transmission module 4 connects with the first rotational drum and the second rotational drum to drive rotations of the first and the second rotational drums simultaneously for switching and synchronizing the excitation filters 12 and the emission filters 31 to match specific wavelengths of the targeted fluorescent probes.

Figure 4:
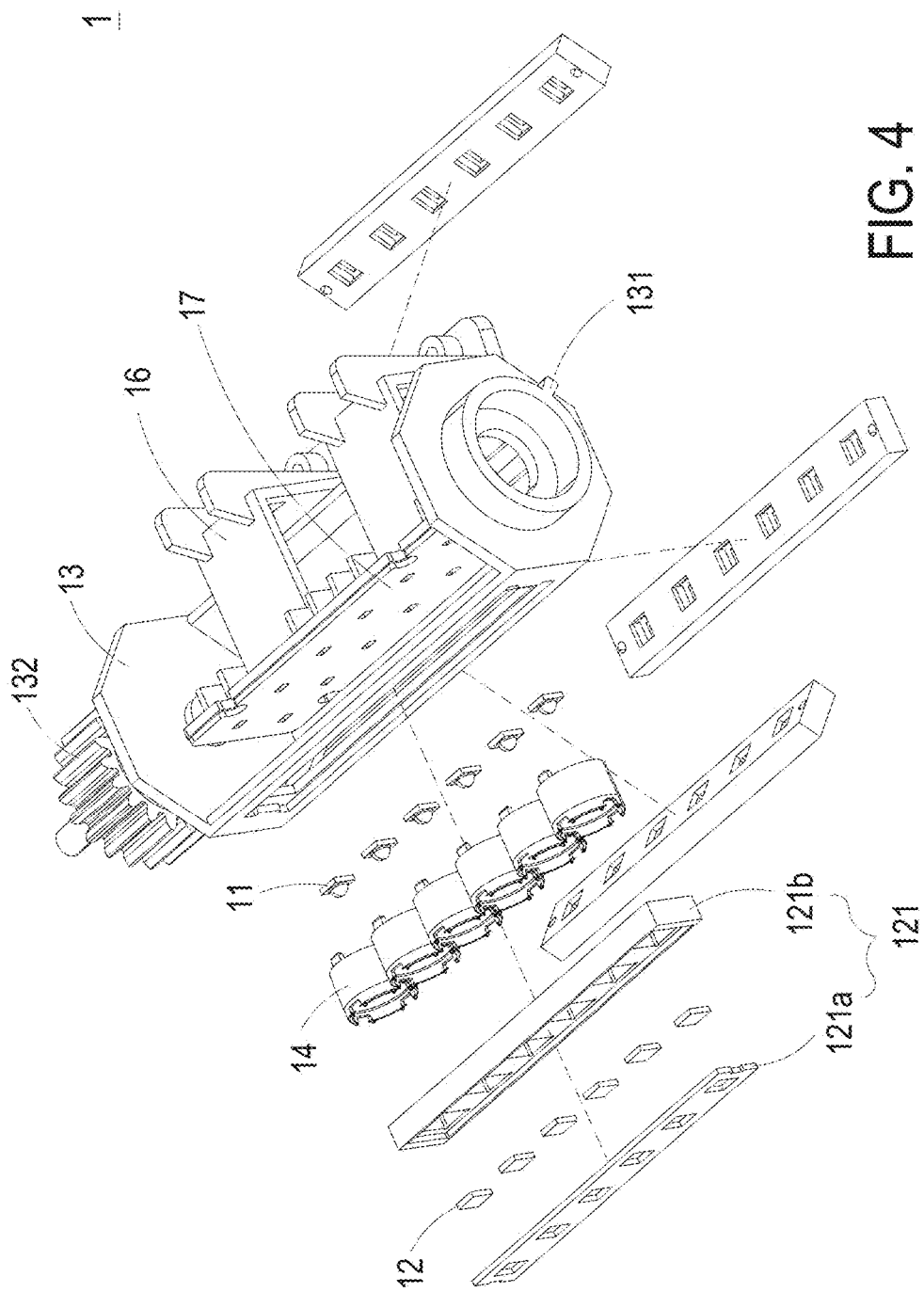
FIG. 4 shows an exploded view of the illumination module.

Please refer to FIGS. 3-4, wherein FIG. 4 shows an exploded view of the illumination module. The light source 11 emits light within a broad band of wavelengths in visible wavelengths, e.g. between 380 nm to 780 nm covering the targeted excitation wavelengths. In an embodiment, the light source 11 is a high power white light LED, which provides optical power in 122 lumens at 350 mA, and its viewing angle at full-width at half maximum (FWHM) is 115 degree. However, the light source 11 is not limited to the white light LED, and any kind of broad-band light source, such as Mercury Lamp, Halogen Lamps, etc. are also applicable.

Figure 5B:
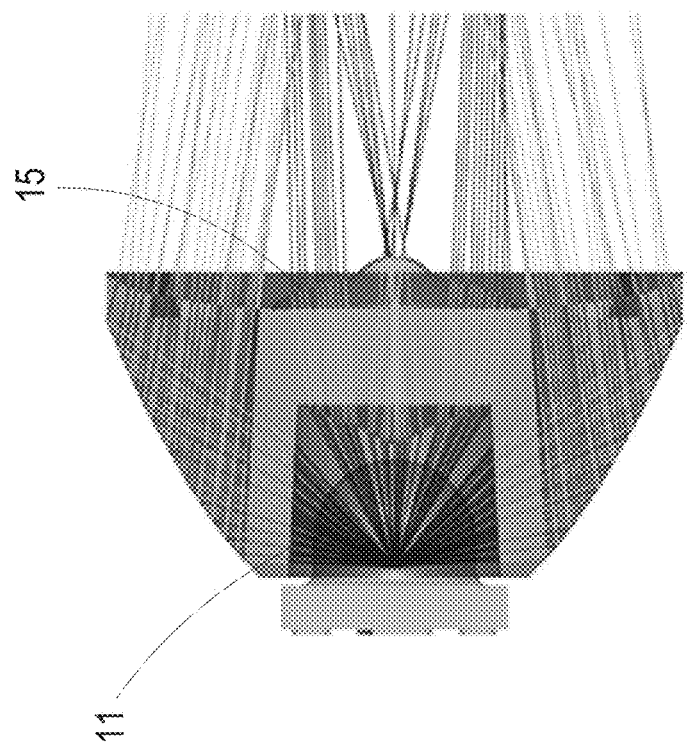
FIG. 5B shows light paths travel through the collimating lens.
Figure 5A:
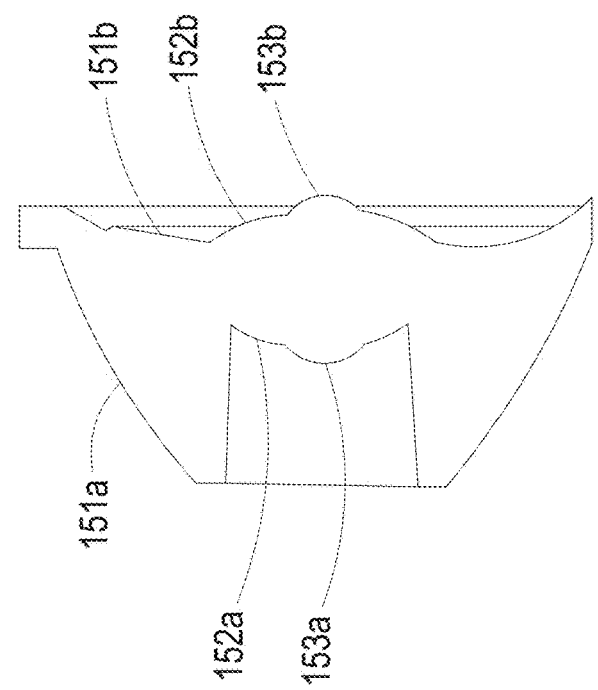
FIG. 5A shows a schematic view of the collimating lens.

In an embodiment, the illumination module 1 includes six lampshades 14. As shown in FIG. 3, each lampshade 14 accommodates one light source 11 and one collimating lens 15 therein, and is required to bend the beam of the light source 11 to be parallel for uniform illumination. FIG. 5A shows a schematic view of the collimating lens, and FIG. 5B shows light paths travel through the collimating lens. The collimating lens 15 is mounted between the light source 11 and the excitation filter 12 and provides light beam deviating in a small angle. The collimating lens 15 is divided into three annular zones, and the optical surfaces 1a to 3b of the collimating lens 15 are the free-form surfaces for the optimal performance. The first annular zone includes the surfaces 151a and 151b, the second annular zone includes the surfaces 152a and 152b, and the third annular zone includes the surfaces 153a and 153b. The light beams travel in the first annular zone hit the surface 151a first, and they will not penetrate through the surface 151a because of total internal reflection. Then the reflected beams hit the surface 151b, and the reflected beam transmitting through the surface 151b will then be bent. The refractive beams going out the surface 151b then become a collimating beam. Light beams traveling in the second annular zone will converge through the surface 152a, and then bend inward even more after coming out of the surface 152b, and thus, the deviation angle of the light beams traveling in this area is about 5 degree closing to collimating beam. In the central area, the third annular zone, the light beams are focused between the surfaces 153a and 153b. For the light beam focusing on the focal spot of the surface 153b, the outgoing beams are parallel to the optical axis of the lens.

In an embodiment, the collimating lens 15 is smaller in diameter (8 mm), has stronger optical power (17 lumens), better optical efficiency (19.8%), and smaller intensity angle (10.2 degree) than the commercial collimating lenses FP11055 sold in the market.

In an embodiment, the material of the collimating lens 15 is but not limited to acrylic (PMMA), and it could also be other kinds of optical-grade plastic, such as polycarbonate (PC), polystyrene or polyolefin. Injection molding, CNC machining and Diamond-turning methods could be applied to manufacture the collimating lens 15.

Figure 6:
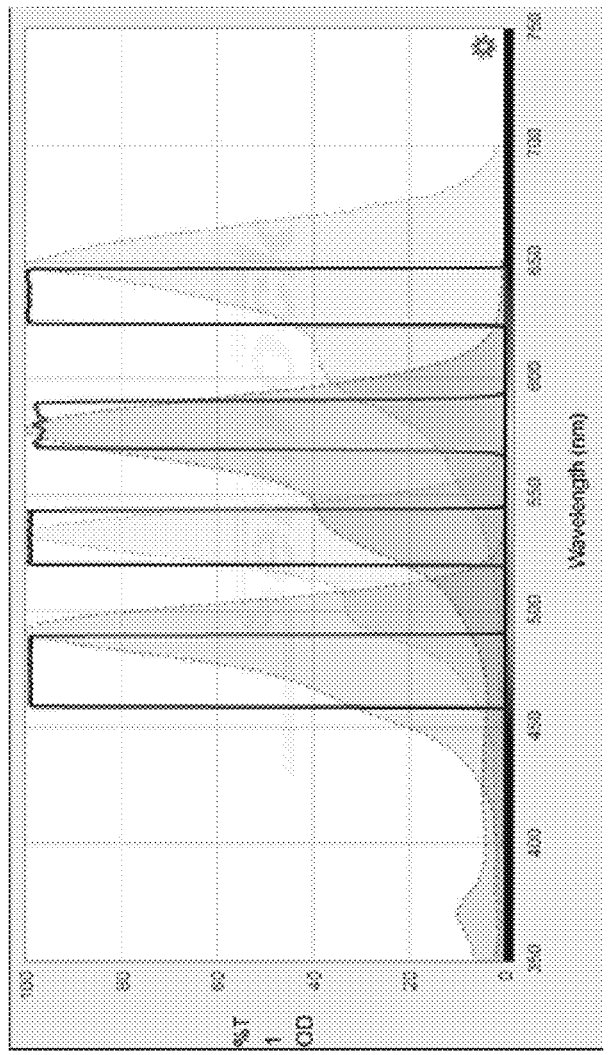
FIG. 6 shows the excitation spectrum of the four types of targeted fluorescent probes and the pass bands of the four types of excitation filters.

Please refer to FIGS. 3-4 again. Depending on the fluorescent dyes labeled on the probes in the PCR samples, four different types of excitation filters 12 are mounted on the first carrier 13 and are selectively to be placed in front of the heating chamber 22. In an embodiment, the excitation filter 12 is a band pass filter which reflects all the incoming light except for the light falls within the pass band. The pass band of the excitation filter 12, therefore, matches the excitation wavelength of the targeted fluorescent probes. In other words, the excitation filter 12 is an optical component that is capable of passing a specific wavelength for excitation from the light source 11, and yet blocking the rest parts of the wavelengths as noise signal. Table 1 shows the pass bands of the four types of excitation filters for exciting four types of fluorescent dyes and FIG. 6 shows the excitation spectrum of the four types of targeted fluorescent probes and the pass bands of the four types of excitation filters. The pass bands of the excitation filters 12 are between 14 nm to 27 nm, so the excitation filters 12 could help to increase the signal to noise ratio (SNR) of the targeted fluorescent probes, and reduce the crosstalk effect which is shown by the overlapped areas of the excitation wavelengths in FIG. 6.

TABLE 1

| Fluorescent Dyes | Excitation Filter | | | |
| --- | --- | --- | --- | --- |
|  | FAM | HEX | ROX | Cy5 |
| Center Wavelength (nm) | 474.3 | 532 | 580 | 635 |
| Pass Band (nm) | 461.0-487.5 | 523-541 | 573-587 | 626.0-644.0 |
| Minimum Bandwidth (nm) | 26.5 | 18 | 14 | 18 |

As shown in FIG. 4, the illumination module 1 further includes a support 16 and a control circuit board 17. The support 16 is used to mount the control circuit board 17 of the light source 11 thereon. In an embodiment, the support 16 is made of aluminum, and is also served as a heat sink for heat dissipation. The light source 11, for example, is a surface-mounted-device (SMD) type LED which is directly mounted on the control circuit board 17 by reflow soldering method, however, through-hole LED is also applicable. In addition, the material of the control circuit board 17 is PCB made of FR-4 glass epoxy, and metal-core PCB (MCPCB) is also applicable for better heat dissipation.

As shown in FIG. 3, the illumination module 1 further includes at least one converging lens 18 mounted between the excitation filters 12 on the first carrier 13 and the heating chambers 22. The converging lens 18 is applied to focus the filtered excitation light beam on the center of the PCR tube. The convergence of excitation light increased the irradiance inside the PCR tube, so the input optical energy received by the fluorescent molecules will be sufficient. In an embodiment, the back working distance of the converging lens 18 is 7 mm from the rear principal plane of the converging lens 18. The converging lens 18 is as simple as a single bi-convex lens made of BK7 glass, and it could also be an assembly of lens sets. In addition, aspheric lens is also applicable, and the lens material could be either glass or plastic. The distance between the excitation filter 12 and the converging lens 18 is around 10 mm.

Figure 7:
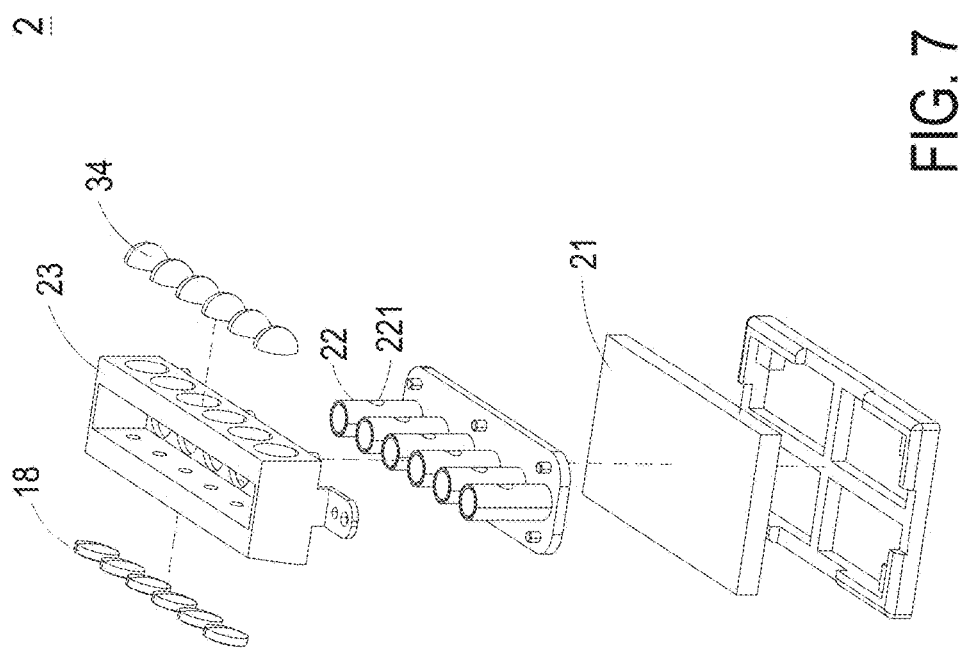
FIG. 7 shows an exploded view of the heating module.

In an embodiment, six converging lenses 18 are mounted linearly on a lens holder 23 sitting on top of the heating chambers 22 (shown in FIG. 7). The first rotational drum of the first carrier 13 rotates freely to switch the excitation filters 12 because the collimating lenses 15 and the converging lenses 18 are mounted separately. The material of the lens holder 23 is black ABS (acrylonitrile butadiene styrene) for its low thermal conductivity, high thermal resistivity, and reduction of internal light scattering.

Please refer to FIGS. 3-4 again. Two rotational drums of the first and the second carriers 13 and 32 are used for switching band pass filters at different wavelengths. The first rotational drum of the first carrier 13 is used for rotating the excitation filters 12, and the second rotational drum of the second carrier 32 is used for rotating the emission filters 31. As shown in FIGS. 3 and 4, the first carrier 13 carries four replaceable filter mounts 121, each of which includes a face plate 121a and a mount body 121b, and six pieces of the excitation filters 12 with the same pass band wavelength are linearly installed right next to each other in the same filter mount 121. In an embodiment, the size of the excitation filter 12 is but not limited to 5 mm×5 mm×2 mm, and it may be varied for different requirement. The filter mount 121 is detachable for the replacement of filters and maintenance. Alternatively, the filter mounts 121 may also be integrated on the first carrier 13.

The multi-channel fluorescence detection device of the present invention includes six optical channels. Each channel requires one piece of the excitation filter 12 and one piece of the emission filter 31, and the arrangement of the excitation filter 12 and the emission filter 31 is linear. When the targeted fluorescent probe changes, the first rotational drum of the first carrier 13 carrying the excitation filters 12 rotates 45 degree in anticlockwise direction one at a time, and the second rotational drum of the second carrier 32 carrying the emission filters 31 rotates the same amount of angle in the same orientation. Aperture windows are designed on both the face plate 121a and the mount body 121b for blocking the incoming beam at large deviation angle. If the incident angle of light is larger than 10 degree, the band pass coating of the excitation filter 12 may not be able to block the light outside the pass band. Those unwanted lights are so called the noise signals, which will interfere with the signal detection. In an embodiment, the size of the aperture window is but not limited to 3.5 mm×3.5 mm, and it may be varied for different requirement.

In an embodiment, the first rotational drum of the first carrier 13 is substantially shaped as an octagonal column, and the four types of excitation filters 12 are mounted on four adjacent rectangular faces of the octagonal column. The first rotational drum of the first carrier 13 further includes a position stop 131 disposed on the side panel of the first rotational drum of the first carrier 13, and a position plate 44 (shown in FIG. 10) disposed on the transmission module 4 is designed for securing the initial position of the first rotational drums of the first carrier 13, so the first rotational drum of the first carrier 13 will not be overturned by the step motor 41 (shown in FIG. 10) of the transmission module 4. The position stop 131 also works as a reference for calibration. Once the position stop 131 hits against the stop 441 on the position plate 44, the step motor 41 will stop to turn.

In an embodiment, the material of the first rotational drum of the first carrier 13 is black anodized aluminum to avoid multiple internal lights scattering in single optical channel and between channels which are two of the sources of the noise signals.

Please refer to FIG. 7, which shows an exploded view of the heating module. The heating module 2 includes the heater 21 and the plural heating chambers 22. Biological samples are prepared and stored in PCR tubes for PCR amplification and detection, and the PCR tubes are held in the heating chambers 22. The pinhole structure 221 of the heating chamber 22 guides the excitation light and emitted fluorescent light to be aligned on the optical axis. In an embodiment, the heating chamber 22 is made of copper for its superior thermal conductivity. The heating module 2 includes six heating chambers 22, and the six heating chambers 22 are positioned linearly for the batch process.

The heating chambers 22 are mounted on the top of the heater 21. In an embodiment, the heater 21 is but not limited to a thermoelectric cooling (TEC) heater. The TEC heater changes temperature in cycle followed by the variation of input current. The temperature control of the TEC heater could be within a fraction of degree, so the requirement of cyclic PCR amplification could be fulfilled. Comparing to other thermal cycler, the compactness of the TEC heater contributes the miniaturization of the system. The TEC heater has long life time, and is easy to maintain. Certainly, other conventional thermal cycling methods through air or liquid are also applicable.

Figure 8:
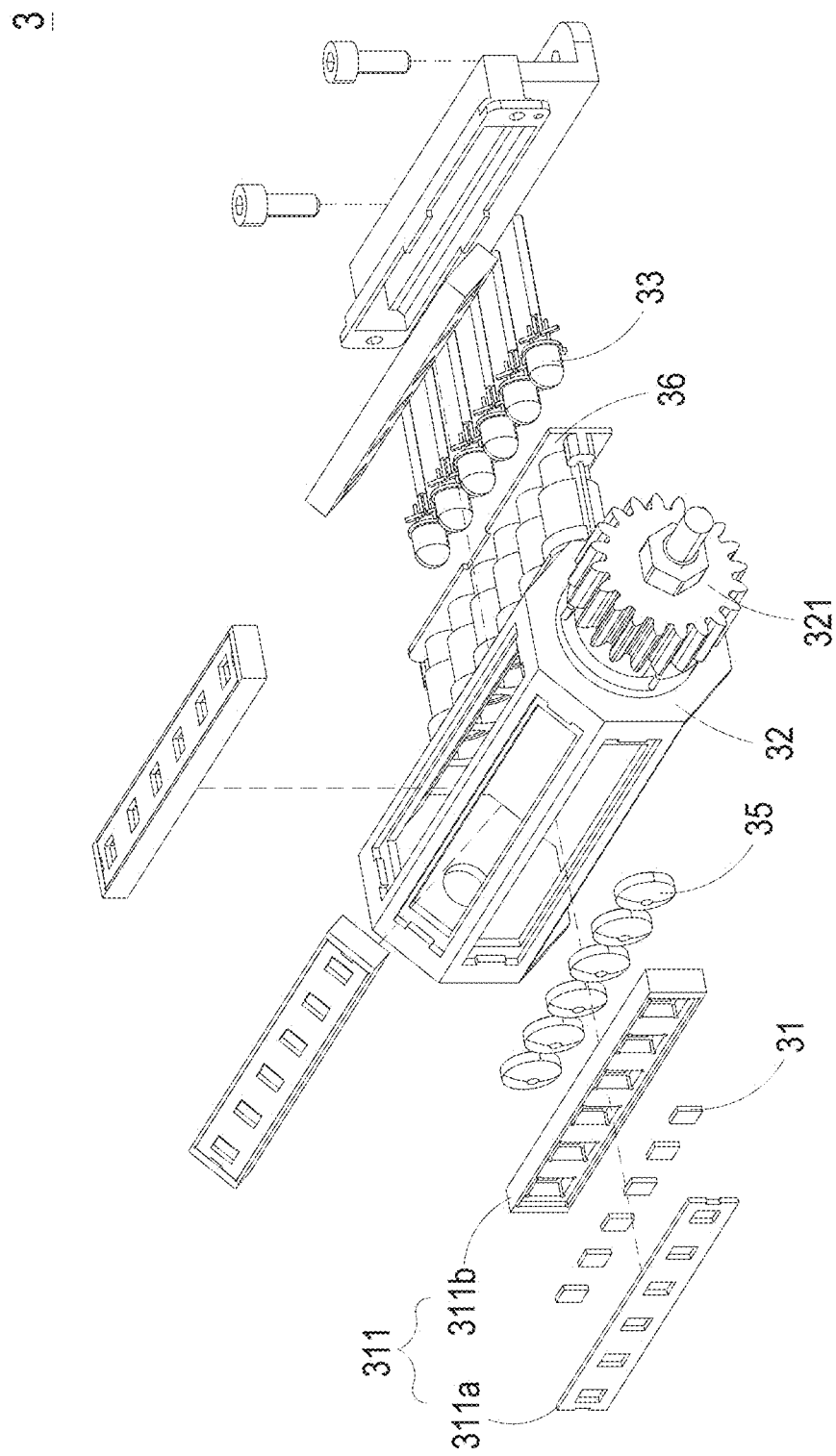
FIG. 8 shows an exploded view of the detection module.

Please refer to FIG. 8, which shows an exploded view of the detection module. Corresponding to the excitation filters 12, there are also four different types of emission filters 31 mounted on the second carrier 32 and are selectively to be placed behind the heating chamber 22. The second carrier 32 carries four replaceable filter mounts 311, each of which includes a face plate 311a and a mount body 311b, and six pieces of the emission filters 31 with the same pass band wavelength are linearly installed right next to each other in the same filter mount 311. In an embodiment, the size of the emission filter 31 is but not limited to 5 mm×5 mm×2 mm, and it may be varied for different requirement. The filter mount 331 is detachable for the replacement of filters and maintenance. Alternatively, the filter mounts 311 may also be integrated on the second carrier 32. The structure of the second rotational drum of the second carrier 32 is similar to that of the first rotational drum of the first carrier 13, and is not redundantly described here.

In an embodiment, the emission filter 32 is a band pass filter which reflects all the incoming light except for the light falls within the pass band. The pass band of the emission filter 32, therefore, matches the emission wavelength of the targeted fluorescent probes. The wavelengths of the fluorescent lights emitted from the fluorescent probes are always longer than their excitation wavelengths, so different filters are required. As the excitation filters 12, the band pass coating of the emission filters only allows light at particular wavelength to go through, and the rest parts of light will be blocked. The emission filters 31 play an important role for preventing the interference of noise signals from the light source 11 and cross-talk effect due to the leakage of the unwanted fluorescent signals.

Figure 9:
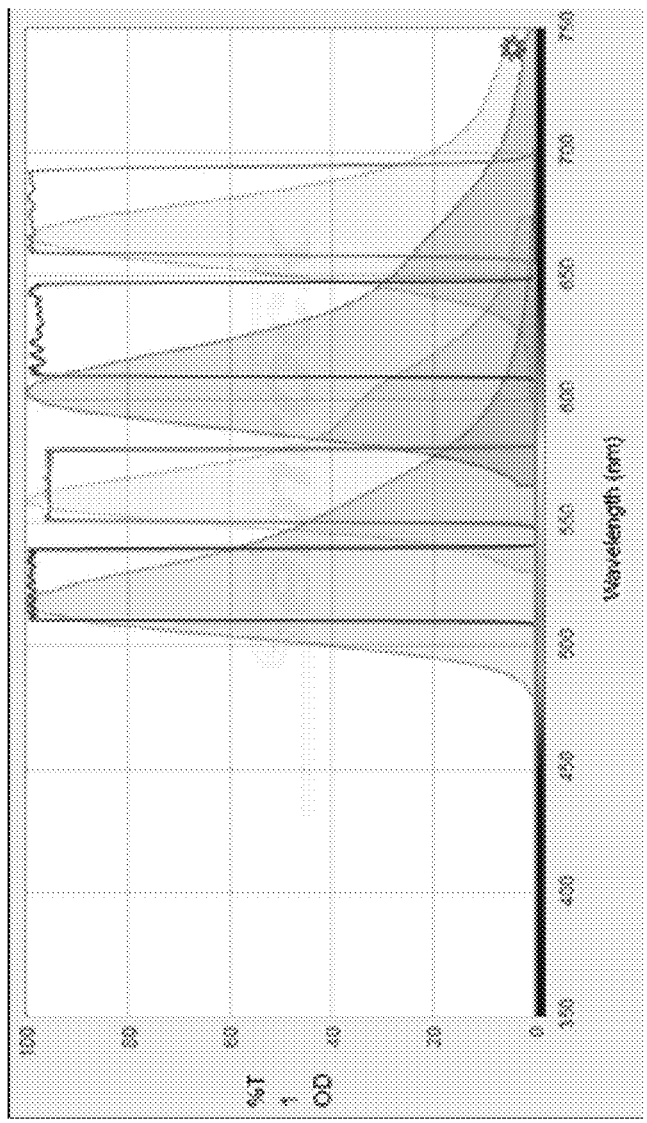
FIG. 9 shows the emission spectrum of the four types of targeted fluorescent probes and the pass bands of the four types of emission filters.

Table 2 shows the pass bands of the four types of emission filters 31 and FIG. 9 shows the emission spectrum of the four types of targeted fluorescent probes and the pass bands of the four types of emission filters. The pass bands of the emission filters 31 are between 24 nm to 32 nm, and the emission filters 31 could help to increase the signal to noise ratio (SNR) of the targeted fluorescent probes, and reduce the crosstalk effect which is shown by the overlapped areas of the emission wavelengths in FIG. 9.

TABLE 2

| Fluorescent Dyes | Emission Filter | | | |
| --- | --- | --- | --- | --- |
| | FAM | HEX | ROX | Cy5 |
| Center Wavelength (nm) | 522 | 565 | 628 | 676 |
| Pass Band (nm) | 510-534 | 553-577 | 612-644 | 661.5-690.5 |
| Minimum Bandwidth (nm) | 24 | 24 | 32 | 29 |

In an embodiment, the photo-detector 33 is a photodiode or a photodiode array, and preferably a silicon photodiode. The photo-detector 33 converts the photo signals to electrical current, and because of its high sensitivity, small numbers of photons of filtered fluorescent light could still be detected from 320 nm to 1100 nm. Other types of photo-detectors, such as photomultiplier tube (PMT), charged-couple device (CCD), and complementary metal-oxide semiconductor (CMOS) are all applicable. In a further embodiment, the detection module 3 further includes a photodiode amplifier, which converts electrical current in few nano ampere to voltage and amplifies the signal up to 10 to the 8 power for further data analysis and utilization.

In an embodiment, the detection module 3 further includes six sets of converging lenses, and each set includes a half-ball lens 34 (shown in FIG. 7) and a bi-convex lens 35 (shown in FIG. 8). The half-ball lens 34 is mounted between the heating chamber 22 and the emission filter 31, and the bi-convex lens 35 is mounted between the emission filter 31 and the photo-detector 33. The number of the detection channels and the number of illumination channels are the same, and each channel of the illumination module maps a corresponding channel of detection module.

The six half-ball lenses 34 are mounted linearly on the lens holder 23 at the opposite side of the six converging lenses 18. The half-ball lens 34 collects fluorescent light emitted from the fluorescent probes in the PCR bio-sample. In an embodiment, the radius of curvature of the half-ball lens 34 is 4 mm, and the plano surface faces the heating chamber 22. The half-ball lens 34 collects the fluorescent light, and transforms it to a collimating beam to evenly illuminate on the emission filter 31. The distance between the sensor of the photodiode 33 and the half-ball lens 34 is about 30 mm.

In an embodiment, the bi-convex lens 35 is made of BK7 glass whose radius of curvature is around 11 mm. The bi-convex lens 35 is disposed behind the emission filter 31 and works as an imaging unit to image the filtered fluorescent light at the image plane which is the sensing surface of photo-detector 33. The bi-convex lens 35 converges the filtered fluorescent light which is uniformly distributed on a large area, and focuses it on the photo-detector 33 whose area, e.g. 1.1 mm×1.1 mm, is much smaller than the distributed area of the filtered fluorescent light. In another embodiment, the material of the bi-convex lens 35 could be optical grade plastic fabricated by injection molds.

In an embodiment, the detection module 3 further includes an electromagnetic (EMI) shielding and grounding structure 36 covering the photo-detector 33 and the bi-convex lens 35. The photo-detector 33 will be influenced by the noise signal from the ambient environment because of its high sensitivity. The EMI shielding and grounding structure 36 is made of aluminum coated with black anodized layer and it could eliminate the EMI noise on the photo-detector 33. The black anodized coating not only prevents the short circuit between positive and negative leads of photo-detector 33, but reduces the internal light scattering inside the optical channel, which is another source of noise signal.

For multi-color qPCR application, the crosstalk effect is a critical issue that needs to be considered. Briefly speaking, when a tube of PCR bio-sample possesses a mixture of multiple fluorescent dyes, the excitation and emission bands of the fluorescent dyes would partially overlap to each other. The overlapped area of the fluorescent bands indicates that the wrong fluorescent dyes are partially excited, and the fluorescent signals emitted from the wrong dyes leak through the emission filter 31. Therefore, the detected fluorescent signal will be a combination of the emission fluorescent signals from different dyes. The emission fluorescent signals coming from the unwanted fluorescent dyes are the noise which reduces the contrast of signal to noise ratio or even causes detection error. The present invention provides an optimal resolution of differentiating targeted fluorescent signal from a mixture of fluorescent probes. Comparing to most of the multi-color qPCR system in the market, the structure of the multi-channel fluorescence detection device of the present invention is smaller and lighter than others. The number of colors illustrated in the present invention for operation is but not limited to four, and it could be up to six.

In an embodiment, four types of the fluorescent dyes are of interest. Each PCR tube is filled with a mixture of four different fluorescent probes. These dyes are standard fluorescent dyes, and their acronyms are FAM/FITC, HEX, ROX, and Cy5. The excitation and emission spectra of the fluorescent dyes are shown in FIGS. 6 and 9, respectively. Although the preferred embodiment of the present invention is described with these dyes, the system of the present invention is not limited to these four types of dyes.

Table 3 shows the crosstalk effect at the mixture of the four types of fluorescent dyes at low concentration (20 nM). It clearly presents that excepting for the filter sets of the specific fluorescent dyes, the emission fluorescent light of other fluorescent dyes are blocked, which indicates that the crosstalk effect of these four types of dyes in this system could be eliminated at low concentrated fluorescent dyes.

TABLE 3

| SNR_20 nM | FAM filter sets | HEX filter sets | ROX filter sets | Cy5 filter sets |
|---|---|---|---|---|
| FITC | 4.20 | 1.04 | 1.00 | 1.00 |
| HEX | 1.47 | 27.98 | 1.19 | 1.11 |
| ROX | 1.30 | 1.12 | 20.65 | 1.13 |
| Cy5 | 1.30 | 1.00 | 1.78 | 8.95 |

Figure 10:
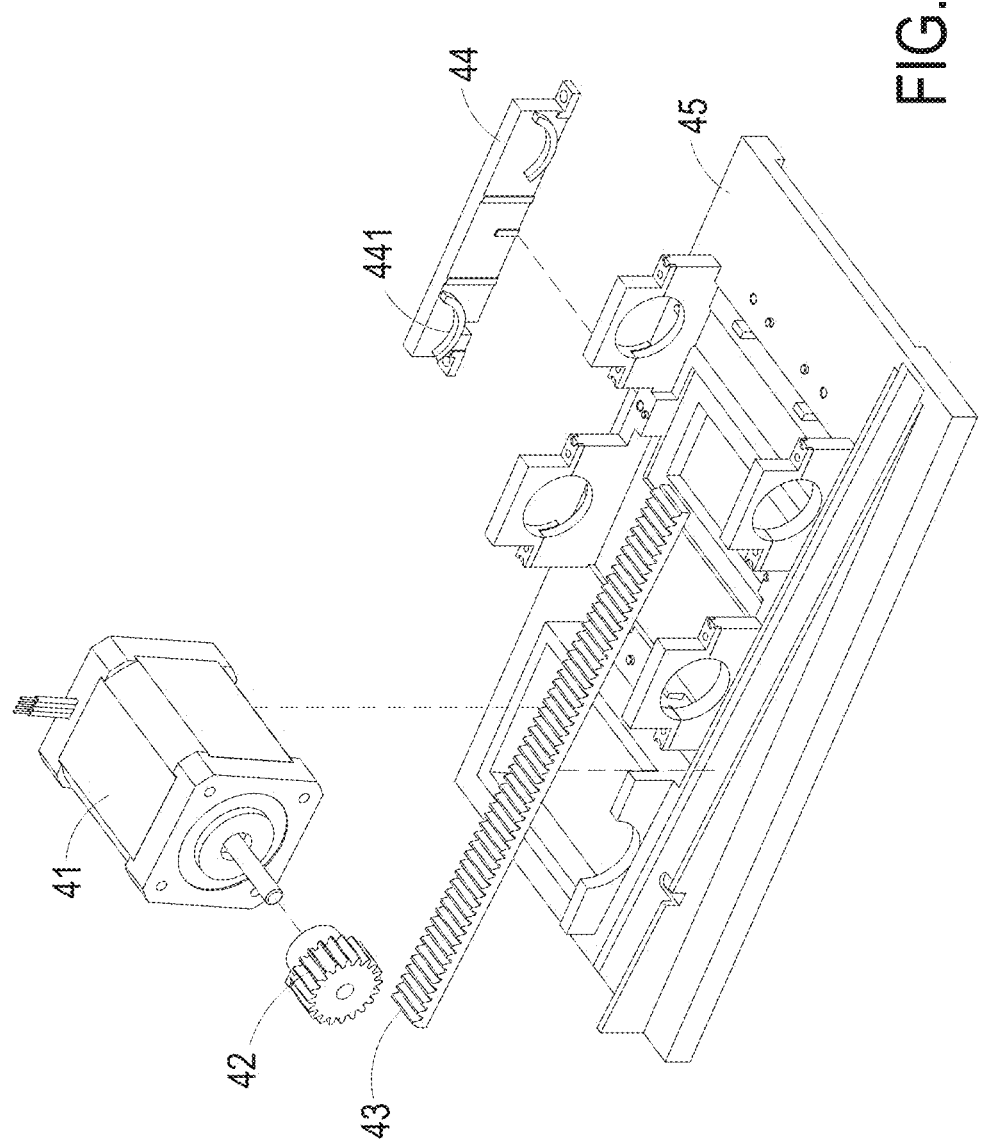
FIG. 10 shows an exploded view of the transmission module.

Please refer to FIG. 10, which shows an exploded view of the transmission module. The actuator of the transmission module 4 is preferably a step motor 41 for driving the rotations of the first rotational drum of the first carrier 13 and the second rotational drum of the second carrier 32 simultaneously. The step motor 31 could provide precise angular change for switching among different filters. This technology has been developed for years in many industries, so the stability and easy access of this technology could accelerate the commercialization of the multi-channel fluorescence detection device of the present invention. Single or dual step motors are both applicable of the present invention. If single step motor is chosen, it is preferably mounted behind the light source 11.

In an embodiment, the transmission module 4 further includes a gear 42 and a rack 43 for power transmission and the synchronization of the first rotational drum of the first carrier 13 and the second rotational drum of the second carrier 32. In other embodiments, a system of gear-sets or the combination of gears and belts are also applicable. The shaft of the single step motor 41 attached with the gear 42 drives the first rotational drum of the first carrier 13 and the second rotational drum of the second carrier 32 simultaneously through the rack 43 and the gear 132 of the first rotational drum of the first carrier 13 and the gear 321 of the second rotational drum of the second carrier 32. While dual step motors are employed, each rotational drum connects to one step motor independently, and the synchronization of two motors is controlled by a motor controlled (MC) circuit.

The step motor 41 utilized in the present invention rotates 45 degree in anticlockwise direction in each step. For four types of filters applied in the present invention, the first and the second rotational drums of the first and the second carriers 13 and 32 will be driven by the step motor 41, and rotate one step at a time. Rotating from the first type of filters to the fourth type of filters, it will rotate 135 degree and stop by the position stops 131 on the first and the second rotational drums of the first and the second carriers 13 and 32 and the stops 441 on the position plate 44.

In an embodiment, the transmission module 4 further includes a base 45 for mounting the step motor 41, the illumination module 1, the heating module 2 and the detection module 3 thereon. The material of the base 45 is but not limited to polycarbonate for its lightweight, robustness, and easy fabrication, and aluminum is also applicable.

In an embodiment, one step motor encoder (not shown) is attached right next to each rotational drum of the first and the second carriers 13 and 32. It will detect the rotation angle of the rotational drum of the first and the second carriers 13 and 32, and feedback a control signal for correction of misalignment and calibration.

Figure 11:
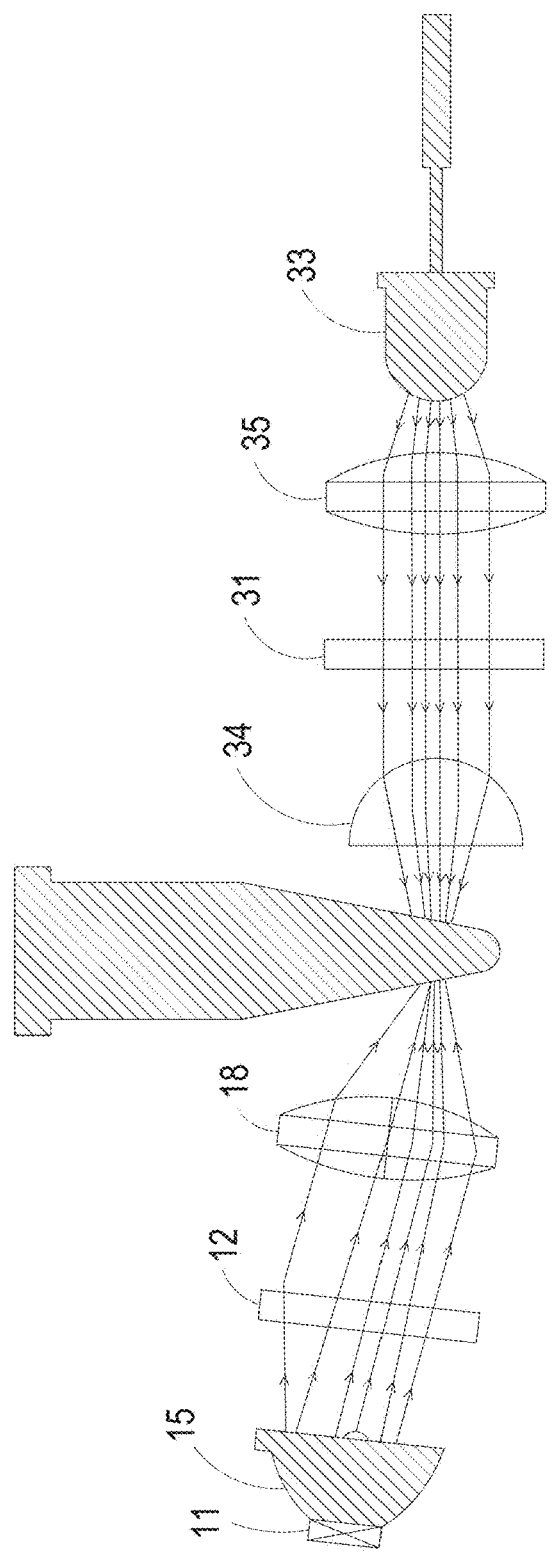
FIG. 11 shows the optical path of the multi-channel fluorescence detection device.

Please refer to FIG. 11, which shows the optical path of the multi-channel fluorescence detection device. The excitation light is provided by a white light LED as the light source 11, and then a collimating lens 15 converges the light to create a uniform and parallel light beam. The excitation filter 12 mounted on the first carrier 13 only passes the collimated beam at particular band width for exciting the targeted fluorescent probes. The converging lens 18, e.g. a bi-convex lens, focuses the filtered excitation light on the PCR tube sitting inside the heating chamber 22. After the PCR sample with the fluorescent probes is stimulated, the fluorescent light at particular wavelength emits out. The emitted fluorescent light is collected by a half-ball lens 34, and illuminated evenly on the emission filter 31 mounted on the second carrier 32. Then the bi-convex lens 35 focuses the filtered emission light on a photodiode as the photo-detector 33. The overall dimension of this optical system is about 105 mm×110 mm×40 mm.

As shown in FIGS. 3 and 11, the separate structure of the collimating lens 15 and converging lens 18 enables the miniaturization of this optical system because the first rotational drum of the first carrier 13 could switch excitation filters 12 in the small gap between these lenses 15 and 18. The spatial usage of the gap between the half-ball lens 34 and the bi-convex lens 35 for the second rotational drum of the second carrier 32 is the same as that on the illumination side. The converging lens 18 and the half-ball lens 34 could be mounted as close as possible to the PCR tube because of the extremely short focal distance of the half-ball lens 34.

As illustrated in the above embodiments, the numbers of the light sources 11, the collimating lens 15, the excitation filters 12 in the same filter mount 121, the converging lenses 18, the heating chambers 22, the half-ball lenses 34, the emission filters 31 in the same filter mount 311, the bi-convex lenses 35 and the photo-detectors 33 are all six. Thus, the multi-channel fluorescence detection device is a six-channel fluorescence detection device. However, the number of the optical channels is certainly not limited to six, and may be varied for different requirement.

In conclusion, the present invention provides the multi-channel fluorescence detection device including the illumination module, the heating module, the detection module and a transmission module. Particularly, the rotations of the two rotational drums are driven simultaneously for switching and synchronizing the excitation filters and the emission filters to match specific wavelengths of the targeted fluorescent probes. The application of the rotational drums ensures the smallest spatial usage for switching different filters without sacrificing large spaces. The rotational drums also provide even illumination on each PCR bio-samples in a batch process, and the tolerance of misalignment of rotational drums is looser than prior arts. Moreover, the technology of step motors has been well developed for years, so the utilization of this technique is easy, cost-efficient, and stable. Finally, if the targeted fluorescent probes are changed, the modularized rotational drums provide an easy way to replace different band pass filter sets.

Further, the design of the excitation and emission filters helps to achieve the compactness of multi-color qPCR system, and according to the present invention, the system is able to provide high signal-to-noise ratio (SNR), and differentiates multiple fluorescent samples at low concentration of 20 nM with minimum crosstalk effect.

In addition, the arrangement of the optical components applied in the present invention improves the uniformity of illumination and the ability of collecting fluorescent light in small space. Besides, because of the well arrangement of optical components, high signal to noise ratio could be achieved, and the performance of detecting fluorescent light signal is still remarkable.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A multi-channel fluorescence detection device, comprising:
    an illumination module including at least one light source, plural different types of excitation filters, and a first rotational drum, wherein the light source provides a broad band illumination, each of the excitation filters passes light at a particular band width for exciting a targeted fluorescent probe, and the first rotational drum drives the excitation filters;
    plural heating chambers adapted for accommodating PCR tubes having samples and the targeted fluorescent probes;
    a detection module including plural different types of emission filters, a second rotational drum and at least one photo-detector, wherein each of the emission filters passes light at a particular band width, the second rotational drum drives the emission filters, and the photo-detector receives fluorescent signals and converts the fluorescent signals to electrical signals; and
    a transmission module including an actuator connecting with the first and the second rotational drums to drive rotations of the first and the second rotational drum simultaneously for switching and synchronizing the excitation filters and the emission filters to match specific wavelengths of the targeted fluorescent probes.

2. The multi-channel fluorescence detection device according to claim 1 wherein the light source is a white light LED.

3. The multi-channel fluorescence detection device according to claim 1 wherein the illumination module further comprises at least one collimating lens located between the light source and the excitation filter.

4. The multi-channel fluorescence detection device according to claim 1 wherein the excitation filter and the emission filer are band pass filters.

5. The multi-channel fluorescence detection device according to claim 1 wherein the illumination module further includes a support and a control circuit board, the light source is mounted on the control circuit board, and the control circuit board is mounted on the support.

6. The multi-channel fluorescence detection device according to claim 1 wherein the illumination module further comprises at least one converging lens mounted between the excitation filter and the heating chamber.

7. The multi-channel fluorescence detection device according to claim 6 wherein the converging lens is mounted on a lens holder sitting on a top of the heating chambers.

8. The multi-channel fluorescence detection device according to claim 6 wherein the converging lens is a bi-convex lens.

9. The multi-channel fluorescence detection device according to claim 1 wherein each of the illumination module and the detection module further comprises plural filter mounts, and the same type of excitation filters or emission filters are installed in the same filter mount.

10. The multi-channel fluorescence detection device according to claim 1 wherein each of the first and the second rotational drum is substantially shaped as an octagonal column.

11. The multi-channel fluorescence detection device according to claim 1 wherein each of the first and the second rotational drum further comprises a position stop disposed on a side panel thereof.

12. The multi-channel fluorescence detection device according to claim 11 wherein the transmission module further comprises a position plate configured to be against the position stops of the first and the second rotational drums for securing initial positions of the first and the second rotational drums.

13. The multi-channel fluorescence detection device according to claim 1 wherein the plural heating chambers are positioned linearly for batch process.

14. The multi-channel fluorescence detection device according to claim 1 further comprising a thermoelectric cooling heater for heating the PCR tubes.

15. The multi-channel fluorescence detection device according to claim 1 wherein the detection module further comprises at least one converging lens mounted between the heating chamber and the emission filter.

16. The multi-channel fluorescence detection device according to claim 1 wherein the detection module further comprises at least one converging lens mounted between the emission filter and the photo-detector.

17. The multi-channel fluorescence detection device according to claim 1 wherein the detection module further includes an electromagnetic (EMI) shielding and grounding structure covering the photo-detector.

18. The multi-channel fluorescence detection device according to claim 1 wherein the actuator of the transmission module is a step motor mounted behind the light source.

19. The multi-channel fluorescence detection device according to claim 18 wherein the step motor rotates 45 degree one at a time.

* * * * *